(12) United States Patent
Vacher et al.

(10) Patent No.: US 12,305,971 B2
(45) Date of Patent: May 20, 2025

(54) STYLUS FOR THREE-DIMENSIONAL SCANNING SYSTEM

(71) Applicants: ONE ORTHO, Saint-Genis-Laval (FR); UNIVERSITE SAVOIE MONT BLANC, Chambery (FR)

(72) Inventors: Pierre Vacher, Chambery (FR); Christian Elmo Kulanesan, Chambery (FR); Ludovic Charleux, Chambery (FR); Emile Roux, Chambery (FR); Christophe Alepee, Saint-Genis-Laval (FR)

(73) Assignees: ONE ORTHO, Saint-Genis-Laval (FR); UNIVERSITE SAVOIE MONT BLANC, Chambéry (FR)

( * ) Notice: Subject to any disclaimer, the term of this patent is extended or adjusted under 35 U.S.C. 154(b) by 0 days.

(21) Appl. No.: 18/540,721

(22) Filed: Dec. 14, 2023

(65) Prior Publication Data
US 2024/0200930 A1    Jun. 20, 2024

(51) Int. Cl.
*G06F 3/03*       (2006.01)
*G01B 11/00*      (2006.01)
*G06F 3/0354*     (2013.01)
*G06F 3/038*      (2013.01)
*G06F 3/041*      (2006.01)
*G06F 3/042*      (2006.01)

(52) U.S. Cl.
CPC ........ *G01B 11/007* (2013.01); *G06F 3/03545* (2013.01); *G06F 3/038* (2013.01); *G06F 3/04186* (2019.05); *G06F 3/0425* (2013.01)

(58) Field of Classification Search
CPC .... A61B 2034/2065; A61B 2034/2068; A61B 2090/3983; A61B 90/39; G01B 11/007; G06F 3/03545; G06F 3/038; G06F 3/04186; G06F 3/0425
See application file for complete search history.

(56) References Cited

U.S. PATENT DOCUMENTS

2017/0325669 A1*  11/2017  Levy ................. A61B 1/00006
2018/0071032 A1    3/2018  de Almeida Barreto
2021/0089140 A1*   3/2021  Thomas, III ........ G06F 3/03542

FOREIGN PATENT DOCUMENTS

KR    2021 0094277    7/2021

OTHER PUBLICATIONS

French Search Report for FR2213876 dated Jun. 28, 2023, in 8 pages.

(Continued)

*Primary Examiner* — Insa Sadio
(74) *Attorney, Agent, or Firm* — Knobbe, Martens, Olson & Bear, LLP

(57) ABSTRACT

A stylus for a manual probing three-dimensional scanning system and viewing system, the stylus including a probe, and a locator comprising a plurality of markers, each marker of the plurality of markers having a normal orientation and a code different from one another, wherein the plurality of markers are of a number, a position, and an orientation such that at least two visible markers of the plurality of markers can be read by a camera of the viewing system from any viewpoint under probing conditions.

16 Claims, 4 Drawing Sheets

(56) References Cited

OTHER PUBLICATIONS

Trinh, Mai et al., "Preliminary Design and Evaluation of an Interfacing Mechanism for Maneuvering Virtual Minimally Invasive Surgical Instruments," International Symposium on Medical Robotics (ISMR), Apr. 13, 2022 IEEE, DOI: 10.1109/ISMR48347.2022.9807585, in 7 pages.

Wu, Po-Chen et al., "DodecaPen: Accurate 6DoF Tracking of a Passive Stylus," UIST, Oct. 22-25, 2017, Quebec City, Canada, in 10 pages.

* cited by examiner

STYLUS FOR THREE-DIMENSIONAL SCANNING SYSTEM

CROSS-REFERENCE TO RELATED APPLICATIONS

The present application claims the priority of French patent application No. FR2213876 ("STYLUS FOR THREE-DIMENSIONAL SCANNING SYSTEM"), filed Dec. 19, 2022, the disclosure of which is incorporated by reference herein in its entirety.

BACKGROUND

Technical Field

The present application relates to the three-dimensional scanning, and more specifically to scanning by manual probing using a stylus surmounted by a passive locator.

Description of the Related Art

Flat markers are widely used in visual spatial location systems. The operating principle consists generally into two main steps:
- detecting the marker on an image; and
- estimating the placement describing the spatial position of this marker.

The markers dedicated to the spatial location are mainly of a binary colour (black and white), square-shaped ("ArUco" contained in the "OpenCV" free library, "AprilTag" developed by the University of Michigan) or bulletin ("CCTag" contained in the eponymous free library). Such markers are constituted of a matrix making it possible to identify the different markers of the locator. The decryption of this matrix is specific to the type of marker used.

A flat marker can be fixed on a movable object in order to monitor the movements of the latter.

In the field of surgical navigation, this marker is positioned on a stylus at the end of which a probe has been fixed. This stylus is used, in order to manually three-dimensionally scan any bone surfaces. It is observed by a camera placed at around 1 metre away.

A phenomenon called "placement ambiguity" appears for certain positions of this marker. In reference to FIG. 1, it is seen that the camera (20) can capture one same image (C1, C1') corresponding to two different positions of the stylus, offset by an angle (b). The scanning system cannot detect if the stylus (10) is in the process of probing a first point (P1) or another point (P1'). Due to the location uncertainties of this marker, it thus becomes difficult, even impossible, to define by monocular vision, the actual placement of the stylus.

In addition, a partially concealed, soiled or also non-flat marker (if it is adhered on a non-flat surface, or if comes off), very strongly affects the spatial position found. The uncertainties of measurements obtained are not compatible with the scanning requirements, and the stylus must be replaced.

SUMMARY

The application therefore aims to overcome the above-mentioned disadvantages, and in particular, aims to propose a stylus making it possible to avoid placement ambiguities.

The application also aims to propose a stylus which is durable.

Finally, the application aims to propose a stylus which is easier to use for the practitioner.

To this end, a stylus has been developed for a manual probing three-dimensional scanning system and viewing system having a probe and a locator comprising several unique markers and each having an orientation normal which is different from one another.

According to the application, the markers are of a number, position and orientation, such that at least two markers can be read by a camera of the viewing system, according to any viewpoint of the locator under probing conditions.

In this way, whatever the position or orientation of the probe, it is guaranteed that several markers will be able to be read by the camera, which makes it possible to avoid placement ambiguities, when a monocular camera is used. In addition, the practitioner does not need to concern themselves about correctly orienting the stylus with respect to the camera: they are therefore freer in their movements during probing, which is facilitated. Moreover, reading two markers instead of one single marker, increases the resolution of the reading carried out: the scanning is more accurate.

By "unique markers", this means that the markers are individual, different from one another.

By "camera", this means any optical capturing device such as a photo device, a camera or a sensor, configured to obtain an image of the markers.

The expression, "according to any viewpoint of the locator under probing conditions", means all the arrangements and inclination of the locator during the probing step which are reasonably predictable, provided the image of the locator being clear (field depth of the compatible camera, and no motion blur during acquisition). Examples of positions are illustrated in FIG. 3.

The locator is passive, i.e. that it emits no light, nor radio waves intended to be captured by the system in order that the latter determines the position of the locator.

In a preferred embodiment, the markers are of a number, position and orientation such that at least three markers can be read by a camera, whatever the position of the marker. This embodiment gives two distinct advantages:
- the information captured by the camera is redundant, as only two markers would have been sufficient for removing placement ambiguity. The redundancy of the information makes it possible to make the estimation of the placement of the stylus even more accurate, therefore the three-dimensional scanning will be of a better quality.
- the durability of the stylus is increased, as if a marker became faulty (either due to soiling during probing, or due to deterioration through wear), then the stylus remains operational, as two markers are sufficient for avoiding placement ambiguities
- the performance of the stylus is increased, as an image captured by the camera can be used, even if the locator is partially concealed (by the surgeon or by any object): it is sufficient that two markers can be seen.

In order to ensure a good readability of the markers, the markers are two-dimensional codes, such as a two-dimensional barcode.

Always to ensure a good readability, for a given viewpoint, the normals of the three visible markers have an inclination less than 75° with respect to the optical axis of the viewpoint, and preferably less than 60°.

In order for the scanning resolution to be good, the probe has a spherical geometry with a radius of between 0.2 mm and 2 mm, and preferably equal to 1 mm.

In another embodiment, the probe has a geometry in the form of a tip, to probe certain articular zones by passing through the cartilaginous zone, in order to touch the bone directly.

In order to ensure a distribution of the markers which is smooth, the normals of the markers are each parallel to the normal of a face of a uniform polyhedron such as a dodecahedron, an icosahedron, a truncated cube or a truncated octahedron. A smooth distribution makes it possible to avoid certain orientations of the locator being less efficient than others.

In an embodiment, the locator has an irregular geometry. This embodiment does not have the abovementioned advantages, however the design and the manufacture of the locator are facilitated, as the geometric constraints are less.

Advantageously, the markers measure between 8 and 20 mm, preferably between 10 mm and 15 mm, and even more preferably, measure 12 mm. By "dimension", this means the length of the sides of a square marker, or the diameter of a circular marker. These dimensions make it possible to have a good compromise between the bulk of the locator and the readability of the markers, when the camera is placed at a distance of around 1 m from the stylus during probing.

The application also relates to a manual probing three-dimensional scanning system and a monocular viewing system, comprising:
a stylus according to the abovementioned features;
a camera configured to acquire an image of the locator during probing;
a computer executing a computer program programmed to:
identify the markers which can be seen on the acquired image;
determine the position of the locator with respect to the camera;
determine the position of the probe with respect to the locator;
reconstruct a geometry of the probed surface from several determined positions of the probe. Such a system makes it possible to benefit from the abovementioned advantages of the stylus. In particular, the stylus according to the application makes it possible to use a monocular camera, which reduces the cost of the system, and which releases the operating field, as there is only one camera viewing field to be identified. The accuracy obtained from the location is however equivalent and sometimes greater than certain existing stereoscopic systems.

The application also relates to a method for calibrating such a viewing system, and comprising the following steps:
the camera acquires several images from the locator according to different viewpoints;
the computer program is programmed to:
identify the markers which can be seen on each acquired image;
three-dimensionally model the relative positions of the markers on the locator;
the position of the probe with respect to the locator being predetermined. Such a method makes it possible to be able to easily use a novel stylus with a preexisting system. The position of the probe with respect to the locator can be determined beforehand, by probing a control with a known geometry.

So as to reduce the memory resources necessary for the computer, the computer program is programmed to evaluate the readability of a marker, so as to either consider the marker during acquisitions (during probing) if its readability is sufficient, or ignore it, if its readability is insufficient. Ignoring it makes it possible to avoid identification errors of the marker and placement ambiguities. Ignoring it also makes it possible to save calculation resources, and the response times of the computer program are improved.

Advantageously, the computer program is programmed to emit an alert when the arrangement of the unreadable markers is such that there are at least two readable markers according to any viewpoint of the locator. This method makes it possible to verify if a stylus is always operational, despite its ageing or deteriorations that it would have been able to suffer.

DETAILED DESCRIPTION

In reference to FIGS. 2 to 8, the application relates to:
a stylus (10) for manual probing making it possible to perform a three-dimensional scanning;
a manual probing scanning system; and
a method for calibrating such a system.

Figure 1:
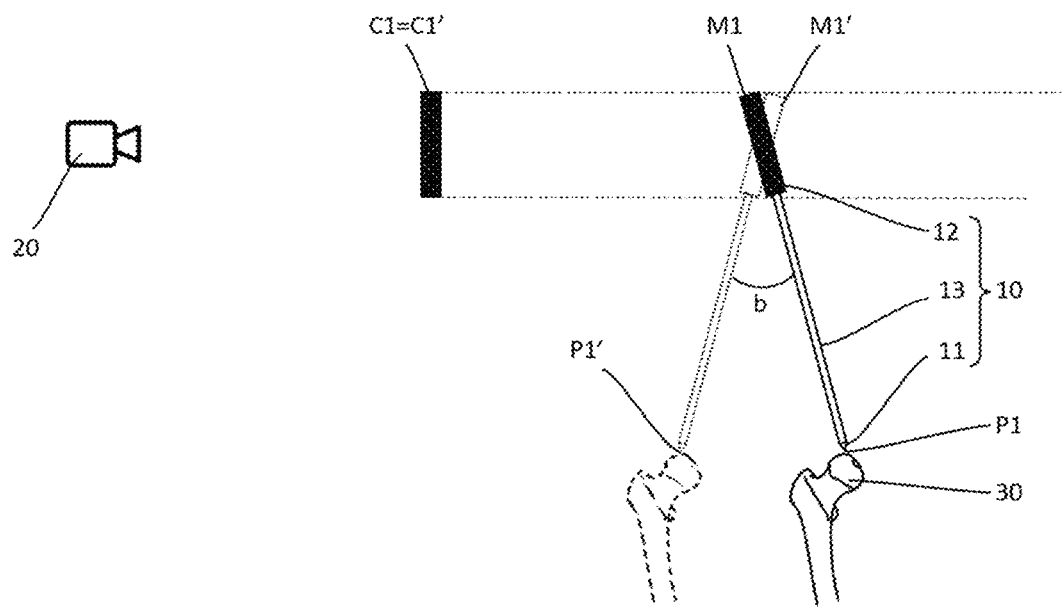
FIG. 1 is a diagram illustrating the placement ambiguities being able to occur with some styluses.
Figure 2:
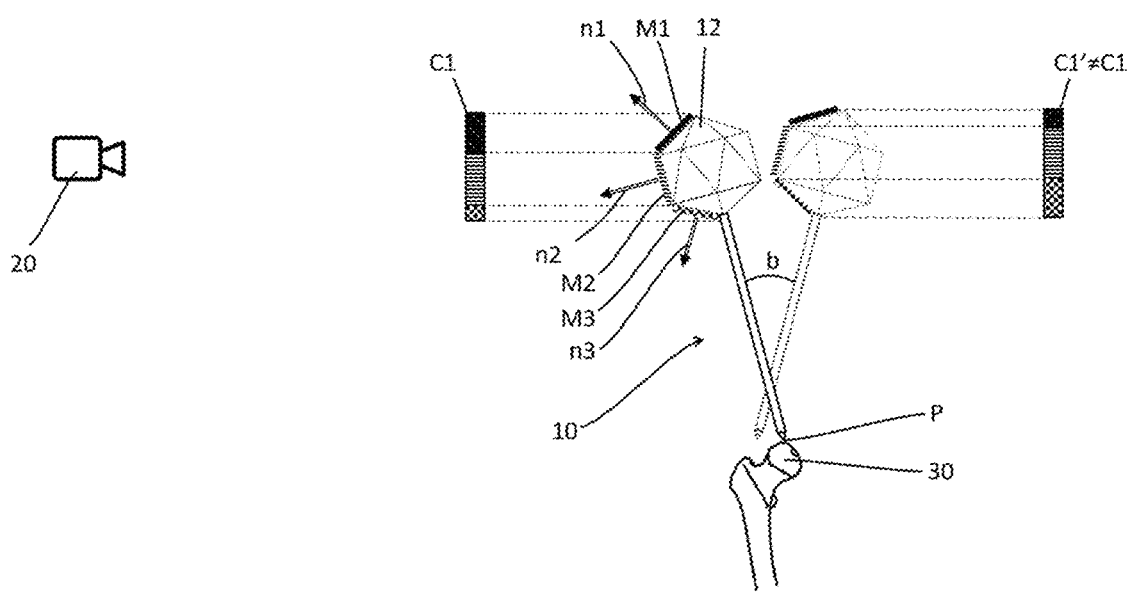
FIG. 2 is a diagram illustrating a stylus.
Figure 3:
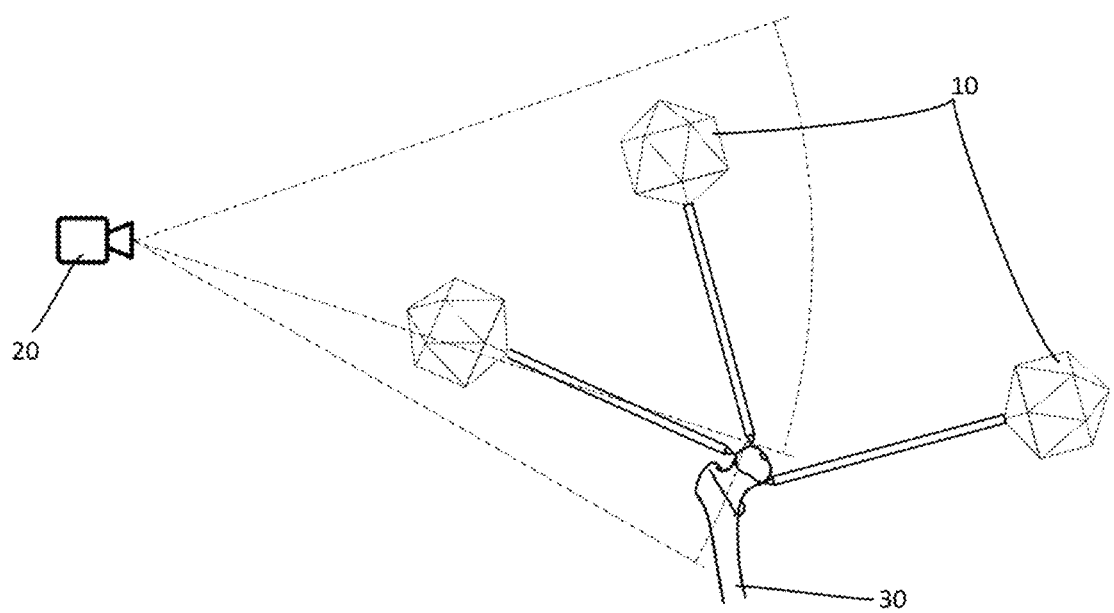
FIG. 3 is a diagram illustrating different positions that a stylus can take during a probing.

In particular reference to FIGS. 2 and 3, a stylus (10) for manual probing scanning comprises:
a probe (11) intended to be positioned on a surface to be scanned of an object (30), for example a part of an articulation;
a locator (12) comprising markers (M), such as dimensional barcodes, intended to be read by a camera (20);
a rod (13) connecting the probe (11) to the locator (12).

According to the relative arrangement of the markers (M), a computer program is programmed to determine the position of the locator (12), and consequently the position of the point on which the probe (11) is placed. Determining a sufficient number of points scanned by this stylus makes it possible to scan the surface of the object (30).

So as to remove any placement ambiguity, the locator (12) has at least two markers (M) which can be read by the camera (20), whatever its position during probing. For this, the locator (12) has markers (M) in suitable number, position, and location.

In FIG. 2, the same angle deviation (b) is reproduced between the inclinations of the stylus (10). A schematisation of the images captured by the camera (20) shows that the capturing (C1) corresponding to the placement on the point (P) cannot be combined with another capturing (C1') corresponding to another inclination.

Consequently, the surgeon is no longer obligated to orient the locator (12) to ensure that the markers (M) actually face the camera (20) during the placement of the stylus (10). It is a lot freer in its movements, which facilitates probing.

FIG. 3 schematically illustrates different positions which a stylus (10) can adopt during a probing. The inclinations of the stylus (10) can be various and varied. With respect to the camera (20), there can be a blind angle disposed behind the object (30) to be probed. In this case, the length of the rod (13) of the stylus (10), generally of between 10 cm and 25 cm, makes it possible to probe this zone, while disposing the locator (12) in the field of the camera (20).

Figure 4:
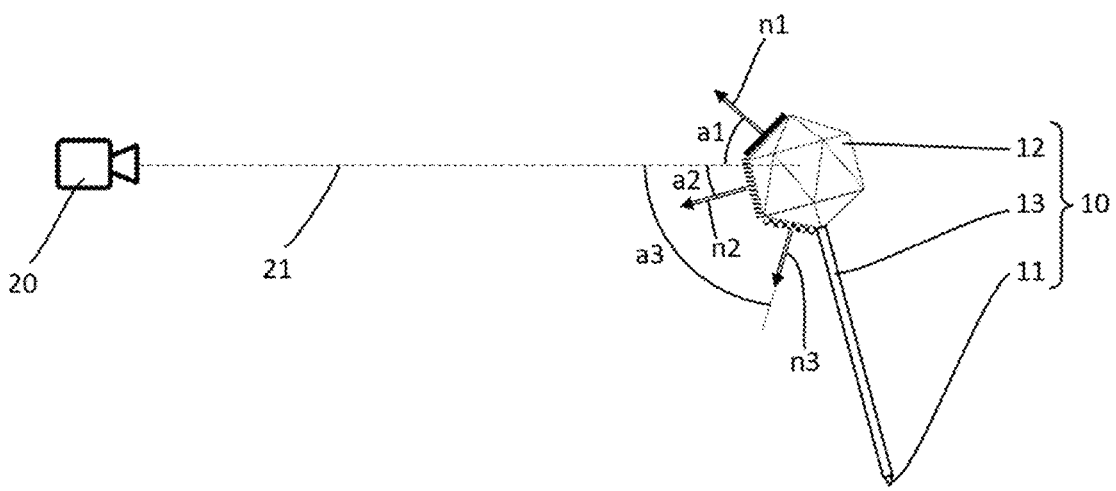
FIG. 4 is a diagram illustrating the inclinations of normals of the markers with respect to the viewpoint of the camera.
Figure 5:
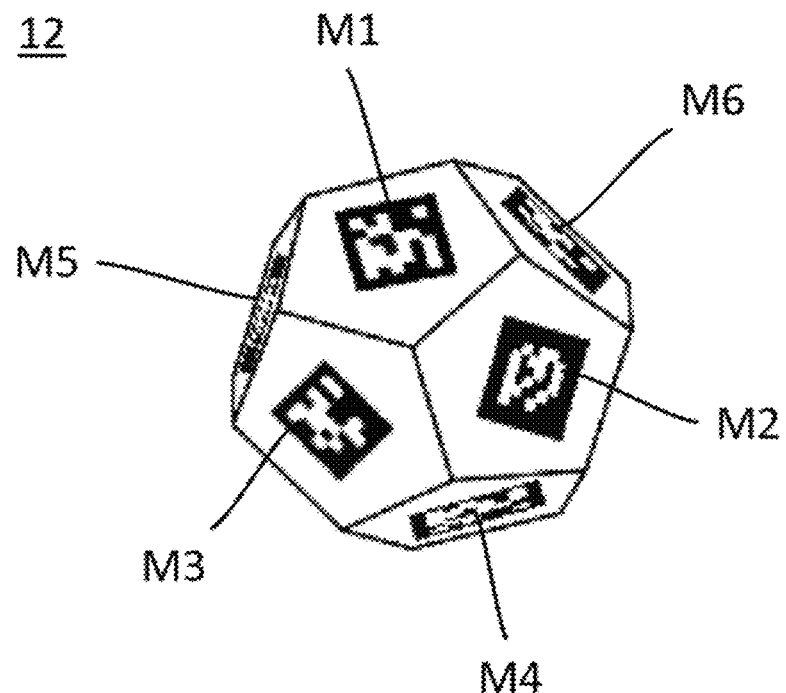
FIG. 5 is a diagram illustrating a locator according to the viewpoint of the camera.

In reference to FIGS. 2, 4 and 5, the orientations that the markers (M) have with respect to the camera (20) are illustrated. The locator (12) has a multitude of markers. Although several markers (M) can be seen by the camera (20), all cannot be read by it.

Indeed, as illustrated in FIG. 4, if a marker (M) has an inclination which is too great with respect to the camera (20), this cannot be read. In FIG. 4:
- the markers (M) M1, M2 and M3 are correctly oriented with respect to the camera (20), such that their readability is possible;
- the markers (M), M4, M5 and M6 are too inclined and cannot be read.

Measuring the inclination of the markers (M) is done between the optical axis (21) of the camera (20), and the normal (n) of the markers. For example, the normals (n1, n2, n3) respectively of the markers (M1, M2, M3) are represented in FIGS. 2 and 4. The corresponding angles (a1, a2, a3) are represented in FIG. 4.

Figure 6:
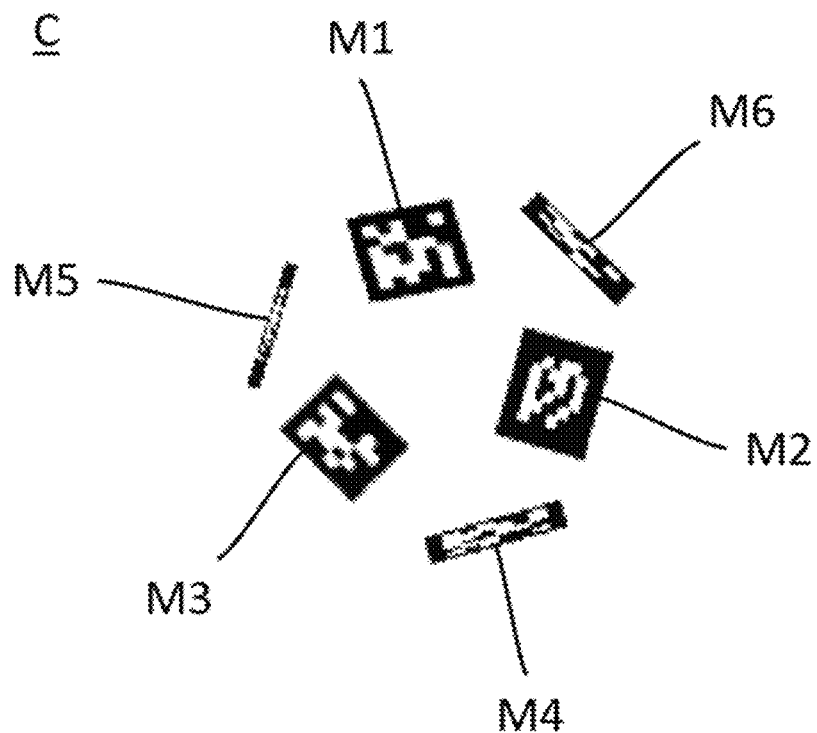
FIG. 6 is a diagram illustrating an image captured by the camera.
Figure 8:
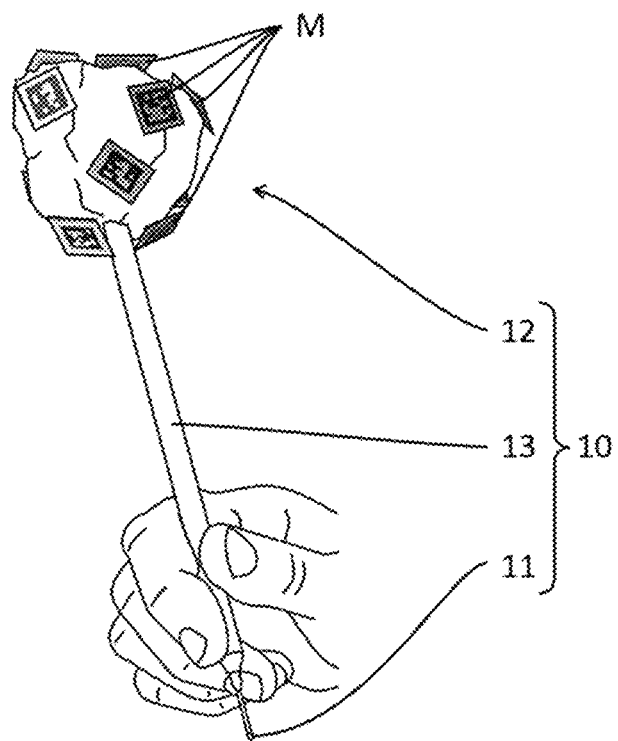
FIG. 8 is a diagram illustrating a stylus, the locator of which is irregularly-shaped.

FIG. 6 illustrates a capturing (C) performed by the camera (20), and makes it possible to illustrate that the problem raised is resolved by the orientation of the markers (M), not necessarily by the geometry such as that of the locator (12):
- the locator (12) can be a convex solid, and in particular a convex uniform polyhedron such as the dodecahedron of FIG. 4, an icosahedron, a truncated cube or a truncated octahedron;
- the locator (12) can be a non-convex solid, for example in the form of a star carrying, at each of its ends, a marker (M): a regular star with twelve branches would provide the same capturing as that of a dodecahedron;
- the locator (12) can be an irregular solid, such as illustrated in FIG. 8.

In practice, a convex uniform polyhedron makes it possible to obtain a regular distribution of the markers (M), such that the reading performance is the same, whatever the orientation of the stylus (10) during probing.

A convex solid does not have retaining zones: the cleaning of the stylus (10) is facilitated, which is preferable in the medical field, and in particular, that of surgery.

Figure 7:
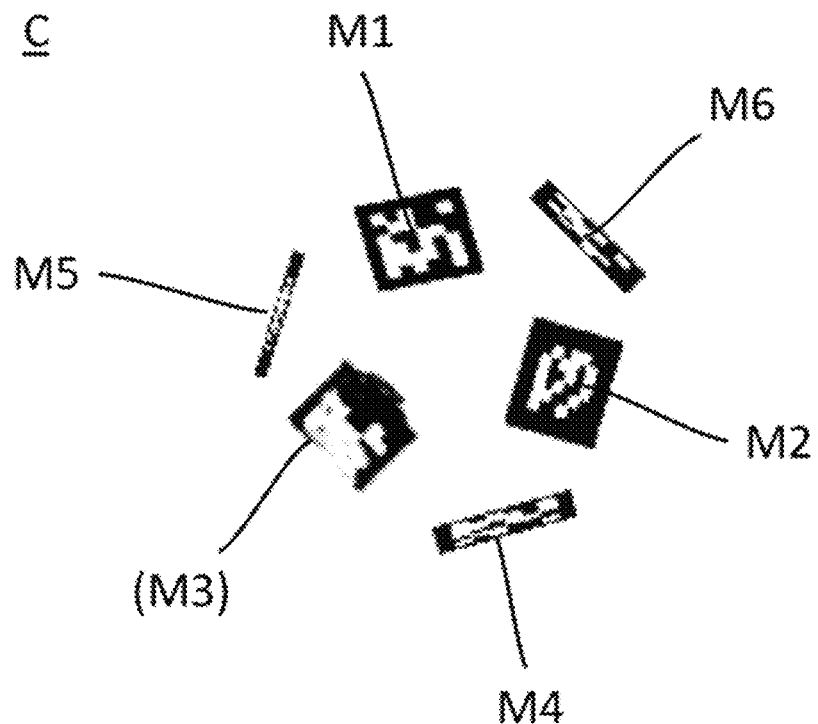
FIG. 7 is a diagram illustrating an image similar to that of FIG. 6, on which a marker cannot be read.

FIG. 7 illustrates a capturing (C) on which a marker (M3) is deteriorated. According to the degradations, a deteriorated marker (M) cannot be read by the program, or also be misread by the program, i.e. to provide:
- a good identification of the marker (M), but in a false orientation; or
- a false identification of the marker (confusion between two markers).

In the case of a false reading, the computer program will be induced in error and the determination of the placement could lead to an ambiguity.

In order to be protected from such disadvantages, a method for calibrating the scanning system comprises a step of evaluating the readability of the markers. During this step, the computer program is programmed to evaluate the readability of each marker (M), so as to:
- either consider the marker (M) during acquisitions, if its readability is sufficient;
- or ignore the marker (M) if its readability is insufficient.

Once the system is calibrated according to this method, the computer program is programmed to not consider the faulty marker (M). This means that on the images captured by the camera (20), the computer program is programmed to ignore the data which can correspond to that of the faulty marker (M). These data are identified by their position with respect to the other markers (M) which can also be read, for example, the markers (M) M1 and M2 in FIG. 6. The risks of placement ambiguities are removed.

The application also relates to a method for calibrating a three-dimensional scanning system, making it possible to be able to use a novel stylus (10) with a preexisting system. This calibration sequence comprises the following steps:
- the camera (20) acquires several images from the locator (12) according to different viewpoints;
- the computer program is programmed to:
- identify the markers (M) which can be seen on each acquired image;
- three-dimensionally model the relative positions of the markers (M) on the locator (12).

Naturally, it is necessary to acquire sufficient images, such that each marker (M) has been viewed at least once by the camera (20).

Thus, for each image captured during probing, the computer program will be capable of identifying the at least two legible markers (M), then of determining the position (including the orientation) of the locator (12).

The position of the probe (11) with respect to the locator (12) being predetermined in the program, the position of the probe (11) can itself also therefore be determined.

Moreover, the calibration method can comprise a step of verifying the conformity of the locator (12). For this, the computer program is programmed to emit an alert when the arrangement of the readable markers (M) is such that there is not at least two readable markers (M) according to any viewpoint of the locator (12). In this way, it is possible to verify that a stylus (10) is always operational (absence of alert), or to replace or to repair the faulty stylus (10) (in case of alert).

A stylus (10) according to the application makes it possible to obtain:
- the position of the probe (11) with an uncertainty less than 1 mm3; and
- the orientation of the rod (13) of the stylus (10) with an uncertainty less than 1°.

The stylus (10) can be located, whatever its position in the observation field, due to the multitude and the arrangement of the markers (M) on the locator (12).

The stylus (10) is compatible just as well with systems comprising several camera (20), as it is with monocular systems.

Moreover, the stylus (10) and the locator (12) can be shaped differently from the examples given without moving away from the scope of the application, which is defined by the claims.

In particular, the markers (M) can be shaped differently from a two-dimensional barcode, can be of any type suitable for the present application. The markers (M) can be of different colours.

Furthermore, the technical features of the different embodiments and variants mentioned above can be, totally or for some of them, combined with one another. Thus, the stylus (10) and the locator (12) can be suitable in terms of costs, functionalities and performance.

A computer system may be implemented in the various embodiments in the described subject matter. The computer system can include a processor, main memory, storage, a bus, and input. The processor may be one or more processors. The processor executes instructions that are communicated to the processor through the main memory. The main memory feeds instructions to the processor. The main memory is also connected to the bus. The main memory may communicate with the other components of the computer system through the bus. Instructions for the computer system are transmitted to the main memory through the bus. Those instructions may be executed by the processor. Executed instructions may be passed back to the main memory to be disseminated to other components of the computer system. The storage may hold large amounts of data and retain that data while the computer system is unpowered. The storage is connected to the bus and can communicate data that the storage holds to the main memory through the bus.

Various embodiments and examples of assemblies have been disclosed. Although the assemblies have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above.

What is claimed is:

1. A stylus for a manual probing three-dimensional scanning system and viewing system, the stylus comprising:
   a probe; and
   a locator comprising a plurality of markers, each marker of the plurality of markers having a normal orientation and a code different from one another;
   wherein the plurality of markers are of a number, a position, and an orientation such that at least two visible markers of the plurality of markers can be read by a camera of the viewing system from any viewpoint under probing conditions.

2. The stylus according to claim 1, wherein the plurality of markers are of a number, a position, and an orientation such that at least three visible markers of the plurality of markers can be read by the camera of the viewing system from any viewpoint under probing conditions.

3. The stylus according to claim 2, wherein the plurality of markers are two-dimensional codes, and wherein for a given viewpoint, normals of the at least three visible markers have an inclination of less than 75° with respect to an optical axis of the viewpoint.

4. The stylus according to claim 3, wherein the normals of the at least three visible markers have an inclination of less than 60° with respect to an optical axis of the viewpoint.

5. The stylus according to claim 1, wherein the probe has a spherical geometry with a radius between 0.2 mm and 2 mm.

6. The stylus according to claim 5, wherein the probe has a spherical geometry with a radius equal to 1 mm.

7. The stylus according to claim 1, wherein normals of the at least two visible markers are each parallel to a normal of a face of a uniform polyhedron.

8. The stylus according to claim 7, wherein the uniform polyhedron is a dodecahedron, an icosahedron, a truncated cube or a truncated octahedron.

9. The stylus according to claim 1, wherein the locator has an irregular geometry.

10. The stylus according to claim 1, wherein each marker of the plurality of markers measures between 8 mm and 20 mm.

11. The stylus according to claim 10, wherein each marker of the plurality of markers measures between 10 mm and 15 mm.

12. The stylus according to claim 11, wherein each marker of the plurality of markers measures 12 mm.

13. A manual probing three-dimensional scanning and monocular viewing system, comprising:
   the stylus according to claim 1;
   a camera configured to acquire an image of the locator during probing; and
   a computer configured to execute computer program instructions to:
      identify the at least two visible markers which can be seen in the acquired image;
      determine a position of the locator with respect to the camera;
      determine a position of the probe with respect to the locator; and
      reconstruct a geometry of a probing surface based upon the position of the locator and the position of the probe.

14. A method for calibrating the system of claim 13, comprising:
   acquiring, by the camera, a plurality of images of the locator from a plurality of different viewpoints;
   identifying, by the computer, the at least two visible markers corresponding to each image of the plurality of images; and
   modeling, by the computer, a three-dimensional model of the at least two visible markers to determine the position of the locator and the position of the probe,
   wherein the position of the probe with respect to the position of the locator is predetermined.

15. The method according to claim 14, wherein the computer is to evaluate readability of each marker of the at least two visible markers to:
   consider the marker if readability of the marker is sufficient; or
   ignore the marker if the readability is insufficient.

16. The method according to claim 15, wherein the computer is to emit an alert when an arrangement of markers having insufficient readability is such that the at least two visible markers does not include at least two readable markers from any viewpoint.

* * * * *

UNITED STATES PATENT AND TRADEMARK OFFICE
CERTIFICATE OF CORRECTION

| | | |
|---|---|---|
| PATENT NO. | : 12,305,971 B2 | Page 1 of 1 |
| APPLICATION NO. | : 18/540721 | |
| DATED | : May 20, 2025 | |
| INVENTOR(S) | : Pierre Vacher et al. | |

It is certified that error appears in the above-identified patent and that said Letters Patent is hereby corrected as shown below:

On the Title Page

Column 1, Line 1, under Prior Publication Data, delete:
"2024"

And insert:
--2024
(30) Foreign Application Priority Data
Dec. 19, 2022 (FR) .... 2213876--.

Signed and Sealed this
Twenty-sixth Day of August, 2025

Coke Morgan Stewart
*Acting Director of the United States Patent and Trademark Office*